United States Patent [19]

Konishi et al.

[11] Patent Number: 4,990,448
[45] Date of Patent: Feb. 5, 1991

[54] BU-4061T

[75] Inventors: Masataka Konishi, Kawasaki; Minoru Hanada; Yuji Nishiyama, both of Tokyo, all of Japan

[73] Assignee: Bristol-Myers Company, New York, N.Y.

[21] Appl. No.: 389,479

[22] Filed: Aug. 4, 1989

[51] Int. Cl.$^5$ .......................... C12P 13/00; C12N 1/00
[52] U.S. Cl. .................... 435/106; 435/825; 435/252.1; 435/53
[58] Field of Search .............. 435/106, 252.1, 53, 435/825,

[56] References Cited

U.S. PATENT DOCUMENTS 4,360,458  11/1982  Koshiyama et al. ............... 435/71.3

Primary Examiner—Herbert J. Lilling
Assistant Examiner—Pamela S. Webber
Attorney, Agent, or Firm—David M. Morse

[57] ABSTRACT

A new antibiotic designated BU-4061T is produced by fermentation of actinomycete strain Q996-17 (ATCC-53904). The BU-4061T antibiotic exhibits both in vitro and in vivo antitumor activity.

2 Claims, 3 Drawing Sheets

1H-NMR SPECTRUM OF BU-4061T

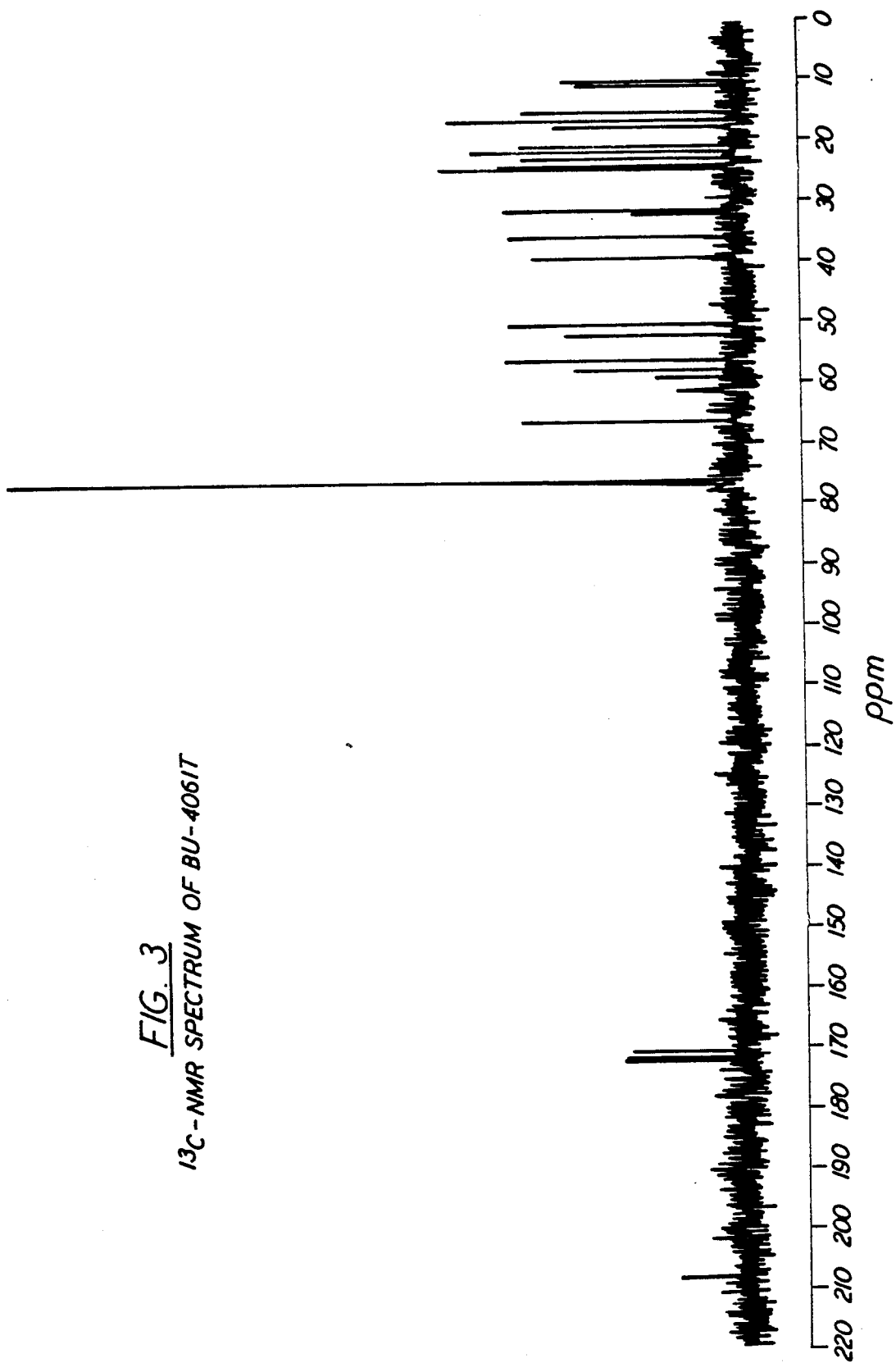

BU-4061T

BACKGROUND OF THE INVENTION

1. Field of the Invention

This invention is directed to a new antitumor antibiotic designated herein as BU-4061T and to a process for the preparation, isolation and purification of BU-4061T in substantially pure form.

2. Description of the Prior Art

U.S. patent application Ser. No. 165,337 filed Mar. 7, 1988 discloses a fermentation antitumor antibiotic designated BU-3862T having the structure

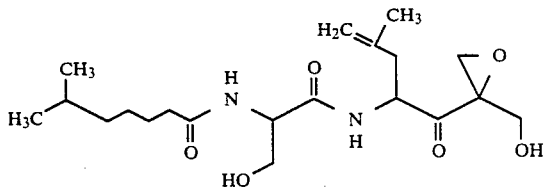

BU-4061T is somewhat related in structure to the above antibiotic.

BRIEF DESCRIPTION OF THE DRAWINGS

FIG. 3 represents the $^{13}$C-NMR spectrum of BU-4061T.

SUMMARY OF THE INVENTION

Figure 1:
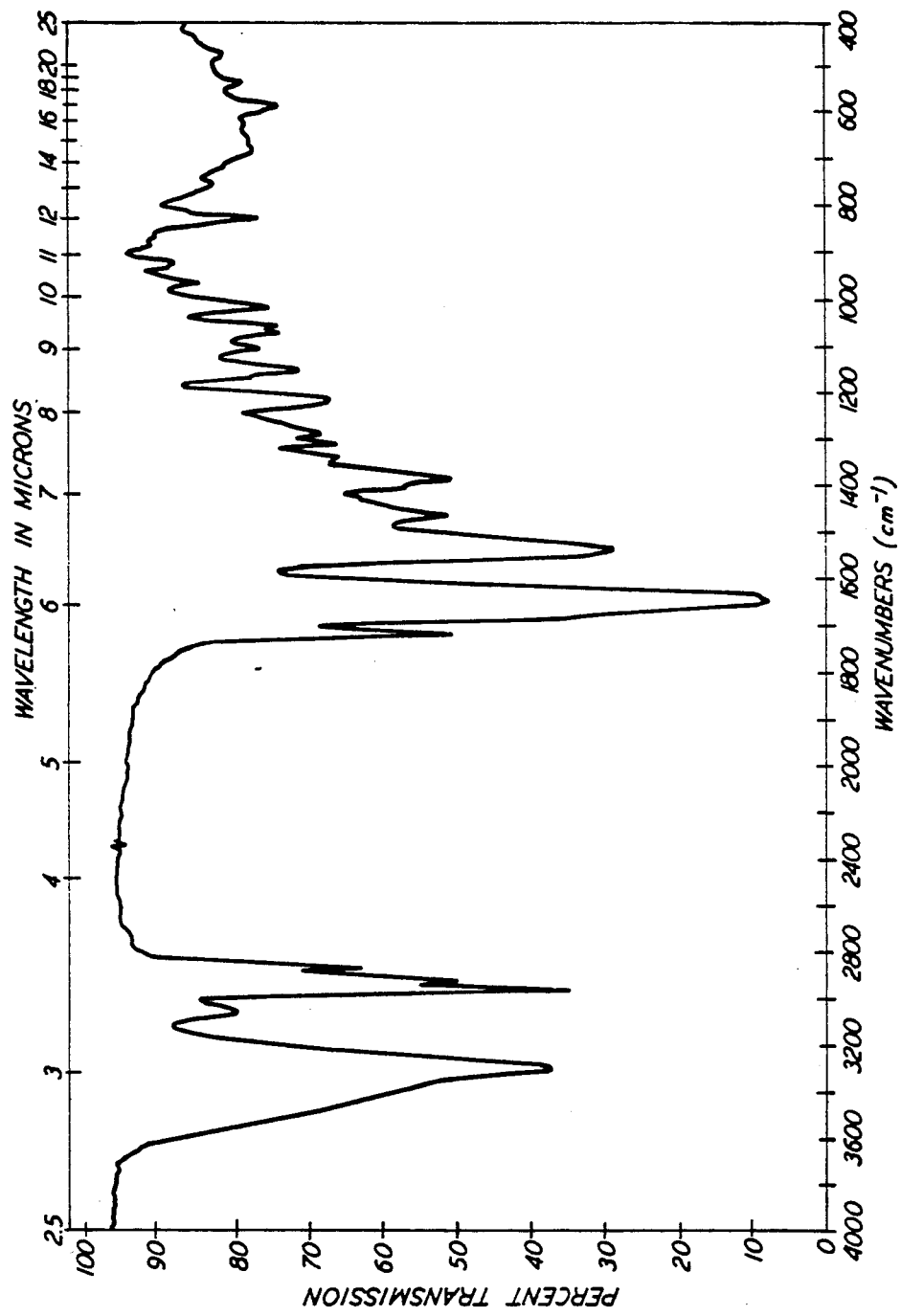
FIG. 1 represents the infrared absorption spectrum of BU-4061T (KBr pellet).

This invention relates to a novel antitumor antibiotic designated BU-4061T and to a fermentation process for preparation of BU-4061T using a new actinomycete designated herein as strain Q996-17 (ATCC-53904). The invention also relates to the new microorganism used in the fermentative production of BU-4061T, use of BU-4061T as an antitumor agent and pharmaceutical compositions of BU-4061T adapted for antitumor use.

DETAILED DESCRIPTION OF THE INVENTION

THE MICROORGANISM

BU-4061T may be produced by fermentation of actinomycete strain Q996-17 or a BU-4061T-producing variant or mutant thereof.

The preferred producing strain designated Q996-17 was isolated from a soil sample collected in Andhra Pradesh State, India.

The cultural and physiological characteristics of the strain were examined by the methods of Shirling & Gottlieb (*Int. J. Syst. Bacteriol.* 16:313–340, 1966) and Gordon et al. (*J. Gen. Microbiol.* 109:69–78, 1978). Diagnostic amino acid and sugar in the whole cell hydrolysate were analyzed by the methods of Lechevalier et al (*Biochem. Syst. Ecol.* 5:249–260, 1977). The menaquinone samples were prepared by the procedures of Collins et al. (*J. Gen. Microbiol.* 100:221–230, 1977) and analyzed with a mass spectrometer. The detection of mycolate and the glycolate test were carried out by the methods of Minnikin et al. (*J. Gen. Microbiol.* 88:200–204, 1975) and Uchida and Aida (*J. Gen. Appl. Microbiol.* 25:169–183, 1979), respectively.

Morphology: Substrate mycelium is long, well-branched and not fragmented into rods or cocci. Aerial mycelium is not formed in ordinary diagnostic media. Rudimentary aerial mycelium is scarcely born in a part of special media such as rabbit dung agar or malt extract-yeast extract agar supplemented with vitamin B complex. These aerial hyphae turn into a coremium (2–30μm width at base) with tapered tip. Sporulation is not observed on the hyphae tip of coremium or other sites of mycelium.

Cultural and physiological characteristics (Tables 1 and 2): The color of substrate mycelium is grayish-olive in organic media, and colorless or light yellow in chemically defined media. Melanoid pigments are not produced. The growth temperature ranges from 19° C. to 45° C. No growth is observed at 48° C.

Cell chemistry: Whole cell hydrolysate contains meso-diaminopimelic acid, galactose, mannose, ribose and rhamnose and hence the strain belongs to cell wall Type III and sugar pattern C. The phospholipids contain phosphatidylethanolamines, phosphatidylglycerol and phosphatidylinositol; therefore, it is placed in Type P-II. The major menaquinone is MK-9 (H$_4$) and MK-10 (H$_4$). Mycolate is absent. Glycolate test is negative.

Taxonomic position: Strain Q996-17 is an aerobic, mesophilic actinomycete, and does not sporulate. Chemotaxonomically, the strain is related to Streptoalloteichus. Saccharothrix and Actinosynnema. However, the strain cannot be placed in any of the above three genera since it is not characterized with sporulative morphology. Thus, strain Q996-17 is best described as an unidentified actinomycete.

A biologically pure culture of actinomycete strain Q996-17 has been deposited with the American Type Culture Collection, Rockville, Md., U.S.A. and added to its permanent collection of microorganisms as ATCC-53904.

It is to be understood that the present invention is not limited to use of the particular preferred strain or to organisms fully answering its description. It is especially intended to include other BU-4061T-producing variants or mutants of the described organism which can be produced by conventional means such as x-radiation, ultraviolet radiation, treatment with nitrogen mustards, phage exposure, and the like.

ANIBIOTIC PRODUCTION

BU-4061T may be produced by cultivating actinomycete strain Q996-17 (ATCC-53904) or a BU-4061T-producing variant or mutant thereof under submerged aerobic conditions in an aqueous nutrient medium. The organism is grown in a nutrient medium containing an assimilable carbon source, for example, trehalose, D-xylose, D-sorbitol, soluble starch, D-ribose, D-melibiose, D-mannose, D-mannitol, maltose, lactose, D-fructose, glycerol, etc. The nutrient medium should also contain an assimilable nitrogen source such as fish meal, peptone, soybean flour, peanut meal, cottonseed meal, corn steep liquor, yeast extract or ammonium salts. Inorganic salts such as sodium chloride, potassium chloride, magnesium sulfate, calcium carbonate, phosphates, etc. are added if necessary. Trace elements such as copper, manganese, iron, zinc, etc. are added to the medium if desired, or they may be supplied as impurities of other constituents of the media.

Production of BU-4061T can be effected at any temperature conducive to satisfactory growth of the producing organism, e.g. 19°–45° C., but it is preferred to conduct the fermentation at 25°–35° C., most preferably 27°–32° C. Production of the antibiotic is carried out generally for a period of about 3 to 7 days.

The fermentation may be carried out in flasks or in laboratory or industrial fermentors of various capacities. When tank fermentation is to be used, it is desirable to produce a vegetative inoculum in a nutrient broth by inoculating a small volume of the culture medium with a slant or soil culture or a lyophilized culture of the organism. After obtaining an active inoculum in this manner, it is transferred aseptically to the fermentation tank medium for large scale production of BU-4061T. The medium in which the vegetative inoculum is produced can be the same as, or different from, that utilized in the tank as long as it is such that a good growth of the producing organism is obtained. Agitation during the fermentation can be provided by a mechanical impeller and conventional antifoam agents such as lard oil or silicon oil can be added if needed.

Production of BU-4061T in the fermentation medium can be readily followed during the course of the fermentation by thin layer chromatography or by a cytotoxicity assay.

Isolation of the BU-4061T antibiotic from the fermentation medium and purification of the BU-4061T may be achieved by conventional solvent extraction and chromatographic techniques. A preferred isolation and purification procedure is illustrated in Example 2 below.

PHYSICO-CHEMICAL PROPERTIES OF BU-4061T

Figure 2:
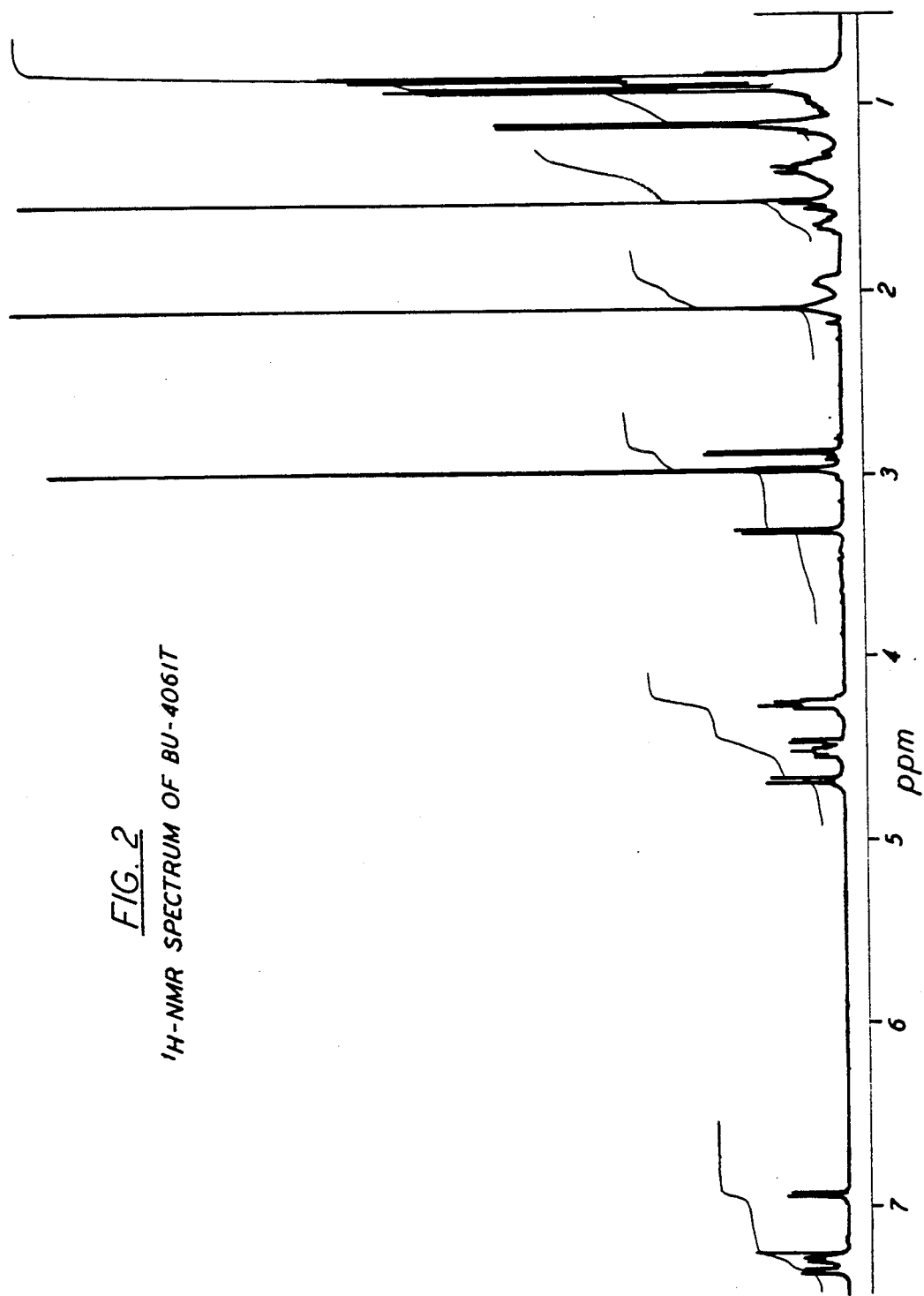
FIG. 2 represents the $^1$H-NMR spectrum of BU-4061T.

BU-4061T was obtained as a white amorphous powder. It was readily soluble in methanol, methylene chloride and ethyl acetate, and practically insoluble in water. BU-4061T gave positive response to iodine vapor, ammonium molybdate-sulfuric acid solution and Rydon-Smith reagent, but negative response to ninhydrin and anthrone reagent. The physico-chemical properties of BU-4061T are summarized in Table 1. The antibiotic did not exhibit characteristic UV absorption. Its IR spectrum in KBr pellet (FIG. 1) showed strong absorptions at 1640 and 1540 cm$^{-1}$, suggesting that BU-4061T belonged to the peptide group of antibiotics. The $^1$H-NMR and $^{13}$C-NMR spectra of BU-4061T are illustrated in FIGS. 2 and 3, respectively. The $^{13}$C-NMR spectrum of BU-4061T demonstrated the presence of 28 carbons including 10 methyl (δ: 10.5, 11.1, 15.5, 15.6, 16.8, 17.8, 21.1, 22.1, 23.3, 32.1), four methylene (24.6, 24.7, 39.5, 52.4), eight methine (25.1, 31.9, 36.2, 50.6, 56.4, 58.0, 61.5, 66.5), one quaternary (59.2) and five carbonyl carbons (170.6, 170.8, 171.7, 172.1, 208.3). The molecular formula of BU-4061T was established as $C_{28}H_{50}N_4O_7$ by the $^1$H- and $^{13}$C-NMR, microanalysis and SIMS (m/z 577 (M+Na)$^+$, 555 (M+H)$^+$).

STRUCTURAL STUDIES

BU-4061T was hydrolyzed with 6N HCl at 105° C. for 17 hours in a sealed tube. The hydrolyzate was diluted with water and extracted with ether. The separated aqueous layer was concentrated in vacuo and lyophilized to yield 158 mg of colorless oily residue which contained three ninhydrin-positive substances by TLC. Two of them were identical with threonine and isoleucine by their TLC and amino acid analysis behavior. This residue was applied on a column of Dowex 50W×4 (H$^+$ type, 100–200 mesh, φ1.5×20 cm), and the column eluted with 0.03N, 0.06N, 0.1N, 0.3N, 0.6N, 1N and 3N of hydrochloric acid, successively. The pooled ninhydrin-positive fractions eluted with 0:06N HCl were concentrated and further chromatographed on a column of Sephadex LH-20 (φ2.2×100 cm) to yield 12 mg of colorless syrup of threonine hydrochloride. The eluate with 0.3N HCl was concentrated in vacuo to give a mixture of isoleucine and an unidentified ninhydrin-positive substance. Separation of them was achieved by a column chromatography on Dowex 50W×4 (pyridine type, 100–200 mesh, φ2.0×75 cm). The unknown amino acid was eluted with 0.1N pyridine-formic acid buffer (pH 3.1). The eluate was concentrated in vacuo and desalted by Sephadex LH-20 chromatography. Evaporation of the appropriate fractions afforded 12.5 mg of white powder. This substance was determined to be N-methylisoleucine by its SIMS spectrum (m/z:168 (M+Na)$^+$, (146 (M+H)$^{30}$) and $^1$H- and $^{13}$C-NMR spectra as shown in Table 2. Isoleucine-containing fractions eluted with 0.2N pyridine-formic acid buffer (pH 3.1) were evaporated in vacuo and the residue was crystallized from aqueous ethanol to give 5.0 mg of colorless needles. The chirality of threonine and isoleucine was determined by using chiral HPLC (TSK gel ENANTIO L1, mobile phase:1 mM CuSO$_4$, detection:254 nm, temperature: 50° C.). The results clearly indicated that both of them has L configuration. The analysis of $^1$H- and $^{13}$C-NMR and $^1$H--$^1$H COSY spectrum of BU-4061T (Table 3) exhibited the presence of the following partial structures in addition to L-threonine, L-isoleucine and N-methylisoleucine.

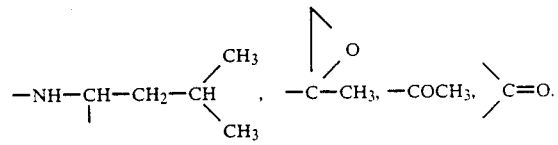

The sequence of these fragments was elucidated by analyzing the $^{13}$C-$^1$H long range COSY and EI-MS spectra of BU-4061T and the structure shown below was assigned to this antibiotic.

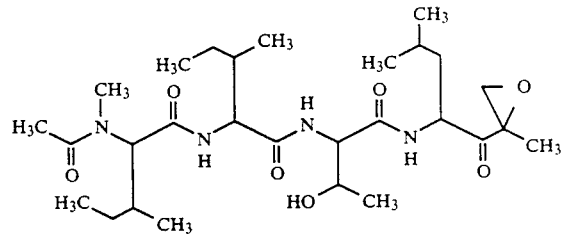

TABLE 1

| Physico-chemical properties of BU-4061T | |
|---|---|
| Nature | White powder |
| M.P. | 107–109° C. |
| [α]$_D$$^{24.5}$ | −66.1 ± 0.4 (c 0.5, MEOH) |
| UV λ$_{max}$$^{MeOH}$ nm | end absorption |
| IR ν$_{max}$$^{KBr}$ cm$^{-1}$ | 3300, 2950, 1720, 1640, 1540 |
| SIMS observed m/z | 577 (M + Na)$^+$, 555 (M + H)$^+$ |
| Microanalysis | |
| Calc'd for C$_{28}$H$_{50}$N$_4$O$_7$ | C 60.62   H 9.09   N 10.10 |
| Found | C 60.45   H 9.15   N 10.18 |
| TLC, SiO$_2$ | CH$_2$Cl$_2$-MeOH   9:1   Rf 0.60 |
| | Hexane-Acetone   1:1   0.27 |

TABLE 2

$^1$H-NMR and $^{13}$C-NMR spectra of N-methylisoleucine $$\overset{5}{CH_3}-\overset{4}{CH_2}-\overset{3}{\underset{\underset{6}{CH_3}}{CH}}-\overset{2}{\underset{NHCH_3}{CH}}-\overset{1}{COOH}$$

| Assignment | Proton (in D$_2$O) δ(ppm), integration (multiplicity, J:Hz) | Carbon (in D$_2$O) δ(ppm), multiplicity |
|---|---|---|
| 1 | — | 173.5, s |
| 2 | 3.48, 1H (d, 4.0) | 69.3, d |
| 3 | 1.93, 1H (m) | 36.6, d |
| 4 | 1.29, 1H (m) / 1.53, 1H (m) | 26.3, t |
| 5 | 0.94, 3H (t, 7.3) | 11.9, q |
| 6 | 0.97, 3H (d, 6.9) | 15.1, q |
| N—CH$_3$ | 2.70, 3H (s) | 33.4, q |

TABLE 3

$^1$H-NMR spectrum of BU-4061T

| δ ppm in CDCl$_3$ | Integration | Multiplicity (J:Hz) | Assignment |
|---|---|---|---|
| 7.36 | 1H | d(7.7) | NH |
| 7.29 | 1H | d(8.1) | NH |
| 6.93 | 1H | d(7.7) | NH |
| 4.68 | 1H | d(11.4) | CH |
| 4.52 | 1H | ddd | CH |
| 4.46 | 1H | dd(2.9, 7.7) | CH |
| 4.26 | 1H | dd | CH |
| 4.24 | 1H | dq(2.9, 6.5) | CH |
| 3.31 | 1H | d(4.9) | CH$_2$ |
| 2.88 | 1H | d(4.9) | |
| 2.98 | 3H | s | N—CH$_3$ |
| 2.11 | 3H | s | CO—CH$_3$ |
| 2.08 | 1H | m | CH |
| 1.96 | 1H | m | CH |
| 1.64 | 1H | m | CH |
| 1.36–1.55 | 2H | m | CH$_2$ |
| 1.51 | 3H | s | $\diagdown$C—CH$_3$ $\diagup$ |
| 1.14–1.36 | 2H | m | CH$_2$ |
| 1.10 | 3H | d(6.5) | CH$_3$ |
| 0.94–1.02 | 2H | m | CH$_2$ |
| 0.92 | 3H | d(3.7) | CH$_3$ |
| 0.90 | 3H | d(3.7) | CH$_3$ |
| 0.82–0.84 | 12H | m | CH$_3 \times 4$ |

BIOLOGICAL ACTIVITY

BU-4061T was tested for in vitro cytotoxicity against murine and human cell lines and for in vivo activity in mice.

B16-F10 (murine melanoma) and Moser (human colorectal carcinoma) cells were grown to the logarithmic phase in the enriched Eagle minimum essential medium supplemented with fetal calf serum (FCS, 10%) and kanamycin (60 µg/ml), while HCT-116 (human colon carcinoma) was grown in McCoy's 5A medium supplemented with FCS (10%) penicillin (100 µ/ml) and streptomycin (100 µg/ml). B16-F10, Moser and HCT-116 cells were harvested and implanted into wells of a 96-well microtiter plate with test materials at the inoculum sizes of $3 \times 10^4$, $6 \times 10^4$ and $6 \times 10^4$ cells/ml, respectively. They were incubated at 37° C. in a humidified atmosphere of 5% CO$_2$ and 95% air for 72 hours. The cytotoxicity against tumor cells was determined colorimetrically at 540 nm after staining viable cells. BU-4061T showed quite potent cytotoxicity against B16-F10 and HCT-116 cells with IC$_{50}$ values of 0.0047 and 0.0067 µg/ml, respectively, whereas the cytotoxicity against Moser cells was weaker than that against B16-F10 and HCT-116 cells (Table 4).

Inhibitory effects of BU-4061T on the macromolecule (DNA, RNA and protein) synthesis were determined in cultured B16-F10 melanoma cells. B16-F10 cells ($10^5$ cells/ml) were incubated with the compound at 37° C. for 4.5 hours (for DNA synthesis) or 4 hours (for RNA and protein synthesis). Labelled precursor, $^3$H-thymidine, $^{14}$C-uridine or $^3$H-leucine was added to the culture and further incubated for 30 minutes (for DNA) or 60 minutes (for RNA and protein). After washing with chilled 5% trichloroacetic acid solution, the radioactivity incorporated into the acid-insoluble fraction of the tumor cells was determined by a liquid scintillation counter. As shown in Table 5, the compound gave moderate inhibitory effects on DNA and RNA syntheses, but it did not significantly inhibit the incorporation of leucine into the protein fraction at the concentration of 100 µg/ml, the highest concentration tested.

To determine in vivo antitumor activity of BU-4061T, male BDF$_1$ mice were intraperitoneally inoculated with 0.5 ml of 10% melanotic melanoma B16 brei, and female CDF$_1$ mice were intraperitoneally inoculated with 0.4 ml of diluted ascitic fluid containing $10^6$ lymphocytic leukemia P388 cells. As shown in Tables 6 and 7, mitomycin C was comparatively used as a reference compound in both experiments. Test materials were intraperitoneally administered to mice on days 1, 5 and 9 (Q4D×3) or on days 1 to 9 (Q1D×9). BU-4061T showed significant antitumor activities against B16 melanoma by either Q4D×3 or Q1D×9 treatment schedule. When tested by Q1D×9 treatment schedule, the compound gave better therapeutic activity in the B16 system than in the P388 system in terms of minimum effective dose and maximum T/C value.

TABLE 4

In vitro cytotoxicity against murine and human tumor cells

| | IC$_{50}$ (µg/ml) | | |
|---|---|---|---|
| Compound | B16-F10 | HCT-116 | Moser |
| BU-4061T | 0.0047 | 0.0067 | 0.17 |

TABLE 5

Inhibition of macromolecule synthesis in B16-F10 melanoma cells

| | IC$_{50}$ (µg/ml) | | |
|---|---|---|---|
| Compound | DNA | RNA | Protein |
| BU-4061T | 16 | 46 | >100 |

TABLE 6

Antitumor activity of BU-4061T against B16 melanoma (ip)

| Compound | Dose (mg/kg/day) | Treatment schedule (ip) | MST*[1] (day) | T/C (%) | Body Wt. change on day 5 (g) |
|---|---|---|---|---|---|
| BU-4061T | 1 | Q1D × 9 | 19.0 | 146*[2] | −1.3 |
| | 0.5 | Q1D × 9 | 19.5 | 150 | −0.5 |
| | 0.25 | Q1D × 9 | 18.0 | 138 | +0.3 |
| | 0.13 | Q1D × 9 | 16.0 | 123 | +1.0 |

TABLE 6-continued

Antitumor activity of BU-4061T against B16 melanoma (ip)

| Compound | Dose (mg/kg/day) | Treatment schedule (ip) | MST*[1] (day) | T/C (%) | Body Wt. change on day 5 (g) |
|---|---|---|---|---|---|
|  | 0.063 | Q1D × 9 | 15.5 | 119 | +0.3 |
| BU-4061T | 4 | Q4D × 3 | 16.5 | 127 | −1.0 |
|  | 2 | Q4D × 3 | 17.0 | 131 | −0.5 |
|  | 1 | Q4D × 3 | 15.5 | 119 | +0.5 |
|  | 0.5 | Q4D × 3 | 15.5 | 119 | −0.3 |
|  | 0.25 | Q4D × 3 | 14.5 | 112 | −0.3 |
| Mitomycin C | 3 | Q4D × 3 | 28.0 | 215 | −0.3 |
|  | 1 | Q4D × 3 | 18.0 | 138 | −0.8 |
|  | 0.3 | Q4D × 3 | 13.0 | 100 | −0.3 |
| Vehicle | — | Q4D × 3 | 13.0 | — | +0.1 |

*[1]Median survival time
*[2]Circle indicates significant antitumor effect (T/C ≧ 125%)

TABLE 7

Antitumor activity of BU-4061T against P388 leukemia (ip)

| Compound | Dose (mg/kg/day) | Treatment schedule (ip) | MST*[1] (day) | T/C (%) | Body Wt. change on day 4 (g) |
|---|---|---|---|---|---|
| BU-4061T | 1 | Q1D × 9 | 10.5 | 105 | −1.3 |
|  | 0.5 | Q1D × 9 | 13.0 | 130*[2] | −1.5 |
|  | 0.25 | Q1D × 9 | 11.5 | 115 | −0.3 |
|  | 0.13 | Q1D × 9 | 11.0 | 110 | −0.5 |
|  | 0.063 | Q1D × 9 | 10.5 | 105 | +0.3 |
| Mitomycin C | 1 | Q1D × 9 | 17.0 | 170 | −0.8 |
|  | 0.5 | Q1D × 9 | 15.5 | 155 | 0.0 |
|  | 0.25 | Q1D × 9 | 13.0 | 130 | +1.0 |
|  | 0.13 | Q1D × 9 | 12.0 | 120 | +1.3 |
|  | 0.063 | Q1D × 9 | 11.0 | 110 | +0.8 |
| Vehicle | — | Q1D × 9 | 10.0 | — | +0.8 |

*[1]Median survival time
*[2]Circle indicates significant antitumor effect (T/C ≧ 125%)

THERAPEUTIC USE

As indicated above BU-4061T exhibits antitumor activity against mammalian malignant tumors.

In one aspect then, the present invention provides a method of treating a mammalian host affected by a malignant tumor sensitive to BU-4061T, which comprises administering to said host a tumor-inhibiting dose of BU-4061T or a pharmaceutical composition thereof.

In another aspect the present invention provides pharmaceutical compositions comprising an effective tumor inhibiting amount of BU-4061T in combination with an inert pharmaceutically acceptable carrier or diluent. Such compositions may contain other antitumor agents and may be made up in any form appropriate for the desired route of administration. Examples of such compositions include solid compositions for oral administration such as tablets, capsules, pills, powders and granules, liquid compositions for oral administration such as solutions, suspensions, syrups or elixers and preparations for parenteral preparation such as sterile solutions, suspensions or emulsions. They may also be manufactured in the form of sterile solid compositions which can be dissolved in sterile water, physiological saline or some other sterile injectable medium immediately before use.

Optimal dosages and regimens of BU-4061T for a given mammalian host can be readily ascertained by those skilled in the art. It will of course be appreciated that the actual dose of BU-4061T used will vary according to the particular composition formulated, the mode of application and the particular situs, host and disease being treated. Many factors that modify the action of the drug will be taken into account including age, sex, weight, diet, time of administration, route of administration, rate of excretion, condition of the patient, drug combinations, reaction sensitivities and severity of the disease.

The following specific embodiments are intended to be merely illustrative and not to limit the scope of the invention.

EXAMPLE 1

FERMENTATION OF BU-40691T

FLASK FERMENTATION

A well grown agar slant of actinomycete strain No. Q996-17 was inoculated to a 500 ml Erlenmeyer flask containing 100 ml of seed medium consisting of soluble starch (Nichiden Kagaku) 2%, soybean meal (Nikko Seiyu) 1% and $CaCO_3$ 0.5% (pH 7 before sterilization). The inoculated flask was incubated at 32° C. for four days on a rotary shaker (200 rpm). Five ml of the culture was transferred to a 500 ml Erlenmeyer flask containing 100 ml of the production medium having the same composition as the seed medium. The fermentation was carried out at 28° C. for six to seven days on a rotary shaker.

The antibiotic production in the fermentation broth was monitored by in vitro cytotoxic activity against B16 melanoma cells. The production reached a maximum after six days of cultivation and cytotoxic activity reached x 256 dilution in terms of MEC (minimum effective concentration).

B. TANK FERMENTATION

A large scale fermentation was carried out in a tank fermentor using the isolate Q996-17-A1 derived from strain Q996-17 using the single colony isolation method. As the seed culture for the tank fermentation, 25 Erlenmeyer flasks (500 ml) were cultivated at 32° C. for three days on a rotary shaker (200 rpm). Two liters of the seed culture were transferred to a 200 L tank fermentor containing 120 liters of the above production medium. The fermentation was carried out at 28° C. with an aeration rate of 120 liters per minute and agitation at 250 rpm. The cytotoxic activity in the fermentation broth reached x 1024 dilution of MEC after a 138 hour fermentation.

EXAMPLE 2

EXTRACTION AND PURIFICATION OF BU-4061T

The whole harvested broth (45 L, pH 8.3) obtained according to the procedure of Example 1 was extracted with n-butanol (16 L) under vigorous stirring. The organic layer was separated with the aid of a continuous centrifuge and evaporated under reduced pressure. The concentrate (1 L) was then extracted twice with 0.7 L each of ethyl acetate. The combined extracts were concentrated in vacuo to an oily residue which was added dropwise to 2 L of n-hexane under stirring. The precipitate which deposited was collected by filtration and dried to give crude solid of BU-4061T (29.9 g). The solid suspended in water (100 ml) was applied on a column of Diaion HP-20 (Mitsubishi Chem. Industries, Tokyo, ϕ4.0×70 cm). Elution was performed with water (3 L), 30% aqueous methanol (3 L), 50% aqueous methanol (3 L) and 80% (4 L) aqueous methanol, successively. The fractions containing BU-4061T were detected by cytotoxicity against B16 melanoma cells. The active fractions eluted with 80% aqueous methanol were evaporated under reduced pressure (4.48 g) and the residue was chromatographed on a silica gel column (φ4.0×50 cm) eluting with methylene chloride/methanol (98:2 v/v). The active fractions were pooled and concentrated in vacuo to afford 442 mg of pale yellow solid. This solid was dissolved in a small volume of ethyl acetate and charged on a silica gel column (φ2.2×50 cm) which was developed with ethyl acetate to yield a semi-pure solid. It was further purified by chromatography on reversed phase silica gel (φ2.2×30 cm). Elution with 55–60% aqueous methanol afforded nearly a homogeneous solid of BU-4061T (124 mg). Final purification was carried out by Sephadex LH-20 chromatography with methanol elution. Evaporation of the relevant fractions gave a homogeneous white powder of BU-4061T (100 mg).

We claim:

1. A process for producing BU-4061T having the formula

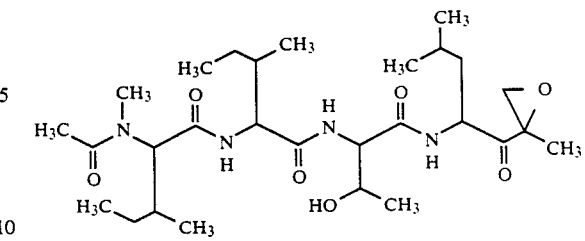

which comprises cultivating actinomycete strain Q996-17 (ATCC-53904) or a BU-4061T-producing mutant or variant thereof in an aqueous nutrient medium containing assimilable sources of carbon and nitrogen under submerged aerobic conditions until a substantial amount of BU-4061T is produced by said organism in said culture medium and then recovering the BU-4061T from the culture medium.

2. A biologically pure culture of actinomycete sp. ATCC 53904, said culture capable of producing the antibiotic BU-4061T in recoverable quantities upon cultivation in an aqueous nutrient medium containing assimilable sources of carbon and nitrogen.

* * * * *